(12) United States Patent
Toth et al.

(10) Patent No.: US 8,237,120 B1
(45) Date of Patent: Aug. 7, 2012

(54) TRANSVERSE FOCUSING ACTION IN HYPERBOLIC FIELD DETECTORS

(75) Inventors: Gabor Toth, San Jose, CA (US); Rudy Garcia, Union City, CA (US); Mehran Nasser-Ghodsi, Hamilton, MA (US); Khashayar Shadman, Mountain View, CA (US); Ming Lun Yu, Fremont, CA (US); Stuart Friedman, Palo Alto, CA (US)

(73) Assignee: KLA-Tencor Corporation, San Jose, CA (US)

( * ) Notice: Subject to any disclaimer, the term of this patent is extended or adjusted under 35 U.S.C. 154(b) by 279 days.

(21) Appl. No.: 12/561,974

(22) Filed: Sep. 17, 2009

Related U.S. Application Data

(60) Provisional application No. 61/099,871, filed on Sep. 24, 2008.

(51) Int. Cl.
*G01N 23/225* (2006.01)
(52) U.S. Cl. ....................................... 250/310
(58) Field of Classification Search ............ 250/306
See application file for complete search history.

(56) References Cited

U.S. PATENT DOCUMENTS

| | | | | |
|---|---|---|---|---|
| 4,764,673 A | * | 8/1988 | Bryson et al. | 250/305 |
| 5,689,112 A | * | 11/1997 | Enge et al. | 850/63 |
| 6,753,261 B1 | * | 6/2004 | Phan et al. | 438/706 |
| 6,972,406 B2 | * | 12/2005 | Syms | 250/281 |
| 7,097,708 B2 | | 8/2006 | Clark et al. | |
| 7,635,842 B2 | | 12/2009 | Nasser-Ghodsi | |
| 2007/0158303 A1 | | 7/2007 | Nasser-Ghodsi | |
| 2007/0194251 A1 | | 8/2007 | Ward et al. | |

FOREIGN PATENT DOCUMENTS

WO WO 99/35668 * 7/1999

OTHER PUBLICATIONS

U.S. Appl. No. 60/099,871 entitled "Tranverse Focusing Action in Hyperbolic Field Detectors" filed Sep. 24, 2008.

M. Jacka et al. "A fast, parallel acquisition, electron energy analyzer: The hyperbolic field analyzer", Review of Scientific Instrument, vol. 70, No. 5, May 1999 pp. 2282-2287.

* cited by examiner

*Primary Examiner* — David A Vanore
*Assistant Examiner* — Eliza Osenbaugh-Stewart
(74) *Attorney, Agent, or Firm* — Joshua D. Isenberg; JDI Patent

(57) ABSTRACT

A defect may be characterized using primary radiation directed from a primary electron source to a measurement location on the sample. An electron energy analyzer may capture secondary electrons emitted from the measurement location in a focusing direction by an electron energy analyzer. A transverse focusing device may focus electrons emitted from the measurement location in a transverse direction that is perpendicular to the focusing direction.

13 Claims, 4 Drawing Sheets

US 8,237,120 B1

TRANSVERSE FOCUSING ACTION IN HYPERBOLIC FIELD DETECTORS

CLAIM OF PRIORITY

This application claims the priority benefit of provisional application No. 61/099,871 to Gabor Toth et al. entitled "TRANSVERSE FOCUSING ACTION IN HYPERBOLIC FIELD DETECTORS" filed Sep. 24, 2008, the entire contents of which are incorporated herein by reference.

CROSS-REFERENCE TO RELATED APPLICATION

This application is related to commonly-assigned co-pending application Ser. No. 12/032,526, filed Feb. 15, 2008 and provisional application 60/890,512, filed Feb. 19, 2007, the entire disclosures of both of which are incorporated herein by reference.

FIELD OF INVENTION

This invention generally relates to an electron energy analyzing system and more particularly to an electron spectrometer, which utilizes a one-dimensional focusing field.

BACKGROUND OF THE INVENTION

Over the past few years, the demand for ever cheaper and lighter weight portable electronic devices has led to a growing need to manufacture durable, lightweight, and low cost electronic circuits including high density memory chips. The increasing complexity of electronic devices and integrate circuits, coupled with the decreasing size of individual circuit elements, places ever more stringent demands on fabrication processes, particularly with respect to resolution and accuracy of the fabrication patterns. The ability to fabricate on a nanometer scale guarantees a continuation in miniaturization of functional devices. Micro-fabrication techniques can produce structures having features on the order of nanometers. Micro-fabrication is used in a wide variety of applications, such as the manufacturing of integrated circuits (i.e., semiconductor processing), biotechnology, optical technology, mechanical systems, and micro-electro-mechanical systems ("MEMS").

Micro-fabrication is typically a multi-step process involving the patterned deposition or removal of material from one or more layers that make up a finished device. Micro-fabrication is sensitive to the presence of contaminant particles. In micro-fabrication it is common to inspect a substrate for the presence of contaminants between process steps. As the size of micro-fabricated features decreases, smaller and smaller contaminant particles and films can affect device yield. A number of tools have been developed for detecting contaminant particles. Inspection tools, such as a scanning electron microscope (SEM) are commonly used to inspect a partially fabricated device or wafer containing multiple devices for defects. For certain cases, it may be sufficient to image the defects, e.g., with the SEM and analyze the image to characterize defects. But for many cases, once defects have been detected it is important to chemically characterize them.

Those skilled in the substrate processing arts have long recognized the need for chemical characterization of very small defects. Unfortunately, many of the suggested defect characterization techniques do not provide chemical specific information. For example, Transmission Electron Microscopy (TEM) with energy dispersion x-ray (EDX) or energy-loss spectroscopy has been suggested for characterization of very small defects. Unfortunately, this technique does not provide chemical specific information and further requires a very thin sample for an electron beam to pass through. Scanning tunneling microscopy (STM) in conjunction with I-V curve or scanning near field optical spectroscopy has also been suggested. Although the sample need not be thin, the results do not provide chemical specific information.

An electron spectrometer utilizing a focusing field, such as a cylindrical mirror analyzer, is often used in spectroscopy of charged particles for chemical analysis that makes use of electrons emitted from a substance after being bombarded or irradiated with electrons or ions from a source such as an electron gun. Typical electron spectrometers operate in a scanning mode in which a voltage between two electrodes varies to selectively focus electrons of different energies onto a detector. An electron spectrum may be derived from a scan of detector signal as a function of voltage between the electrodes. Unfortunately, such scanning can take several minutes to complete. During this time, contaminants may build up on the sample and affect the spectrum. Consequently, most electron spectroscopy is done under ultra-high vacuum (UHV) condition ($10^{-10}$ torr or less). However, UHV conditions require expensive equipment and considerable time. Thus, UHV electron spectroscopy is incompatible with semiconductor processing. It is within this context that embodiments of the present invention arise.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Although the following detail description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Figure 1A:
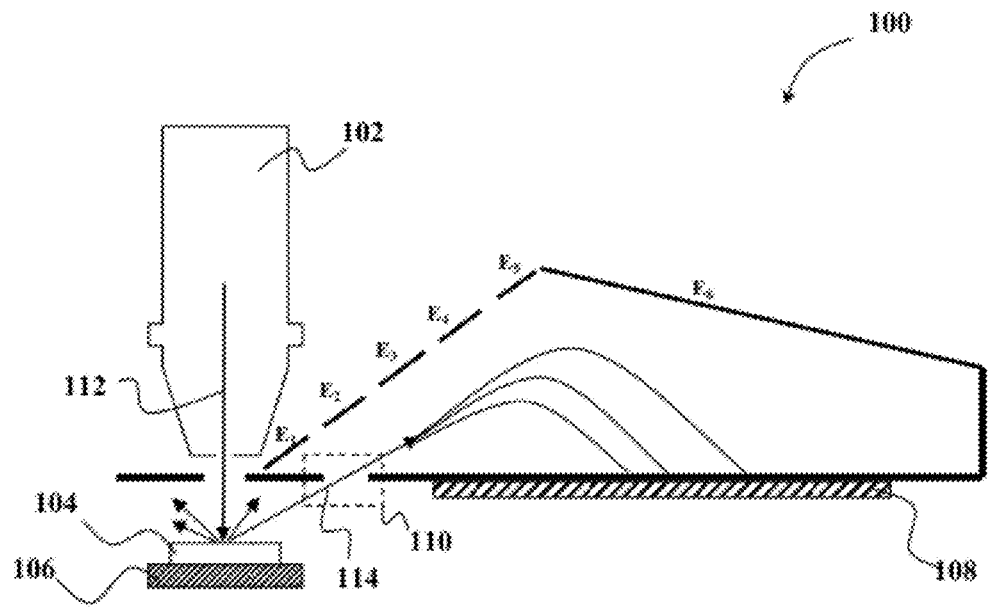
FIG. 1A is a schematic diagram illustrating a hyperbolic field analyzer of a type that may be used in conjunction with embodiments of the present invention.

FIG. 1A is a schematic diagram illustrating a hyperbolic field analyzer 100, which may be used in embodiments of the present invention. Primary radiation 112 from a source 102 (e.g., an electron beam column in the case of Auger, an ultraviolet source in the case of UPS or an x-ray source in the case of XPS) bombards the surface of a sample 104 placed on a sample holder 106. Interaction between the primary radiation 112 and the sample 104 causes secondary electrons 114 to be emitted. Some of the secondary electrons 114 enter the analyzer 100 through an aperture 110, where they are subjected to a substantially hyperbolic electric field, which may be approximated with a small number of electrodes $E_1$ to $E_6$. As shown in FIG. 1A, the electrodes $E_1$ to $E_5$ are arranged in a plane which is inclined to the axis of the detector 108, and the electrode $E_6$ is similarly inclined, but in an opposite direction. Each electrode $E_1$ to $E_6$ is connected via a set of adjustable voltage dividers to a single power supply, allowing on-line control of the shape of the field. More details about hyperbolic fields and hyperbolic field analyzer prototypes can be found in International Publication No. WO 99/35668 entitled "Charged Particle Analyzers" to Prutton et al., filed Jan. 12, 1999, and in "A fast, parallel acquisition, electron energy analyzer: The hyperbolic field analyzer" by M. Jacka et al. in Review of Scientific Instruments Vol. 70, No. 5, May 1999, which are incorporated herein by reference.

An important feature of the electron energy analyzer 100 is the ability to detect electrons over a large range of energy in parallel over an energy range associated with Auger electrons (e.g., about 50 eV to about 2050 eV). In general terms, the substantially hyperbolic field produced by applying appropriate voltages to the electrodes $E_1$ to $E_6$ deflects the secondary electrons 114 to impinge upon a position sensitive detector 108 at different locations depending on secondary electron energy. By way of example, the detector 108 may include a micro-channel plate and a phosphor screen to detect secondary electrons 114 of different energies at different locations. The detector 108 detects electron signals at multiple locations in parallel and produces a separate signal for each location or "channel". Because the signal at each location depends on the energy of electrons 114 that impinge on the detector 108 at that location, the analyzer 100 can obtain a secondary electron energy spectrum in a very short period of time, e.g., on the order of about 1 or 2 seconds. It turns out that this is sufficiently fast because an Auger spectrum could be obtained in a high vacuum environment (about $10^{-6}$ to $10^{-7}$ torr) before more than about 1 to 3 monolayers of adsorbates from background gas would build up on the sample 104. Consequently, the analyzer 100 could be used to chemically characterize defects that are too small to image with an SEM or other imaging technique.

It is noted that certain pre-existing notions of those in charged particle spectroscopy and substrate processing arts would weigh against using the analyzer 100 for chemical characterization of defects in a production-scale processing environment. Specifically, those skilled in charged particle spectroscopy and substrate processing arts associate techniques like Auger spectroscopy with ultra-high vacuum environments, but not high vacuum environments. Thus, those skilled in the substrate processing arts would not expect Auger spectroscopy to work in a production-scale substrate processing environment.

Figure 1B:
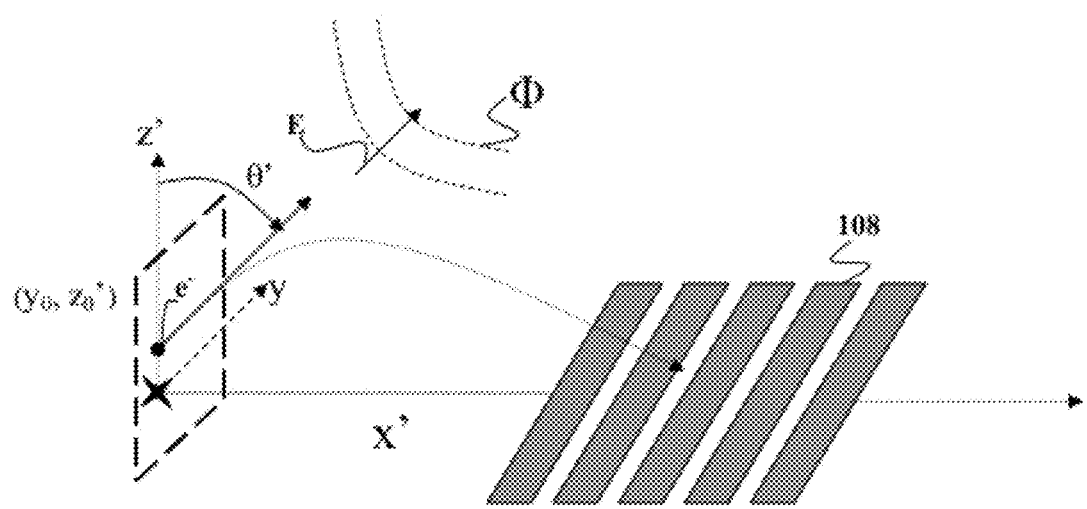
FIG. 1B is a schematic diagram showing trajectories of electrons entering a hyperbolic field energy analyzer.

FIG. 1B is a graph showing the trajectories of the electrons of different energies entering the hyperbolic-field energy analyzer. As seen in FIG. 1B, electrons $e^-$ enter the hyperbolic field energy analyzer 100 through the aperture 110 at a point on the x-axis (the focusing axis) labeled ($y_0$, $z_0$'). The voltages applied to the electrodes $E_1$ to $E_6$ produce electric potential contours $\Phi$ and a corresponding electric field E. The electrons $e^-$ are deflected by the electric field E and follow trajectories that depend on the electron energy.

The hyperbolic electrostatic field is a highly dispersive focusing field (chromatic optics), which focuses generally in a direction along a line connecting the object and the image. This direction will be referred to as the "focusing direction". The direction perpendicular to the focusing direction is referred to herein as the "transverse direction". In the absence of additional focusing fields, the hyperbolic-field deflection system does not control the trajectory of the electrons in the transverse direction originating from the object. Therefore, electrons with a given energy land in a line (approximately) perpendicular to focusing direction. To capture all of these electrons along this line for all energies, current methodology uses wide sensor arrays, which have a lateral size (width) that overlaps with the line of electrons as much as possible. However, the maximum available detector width for commonly available detectors is shorter than the width of the focus line and large sensors are also very expensive.

Figure 2:
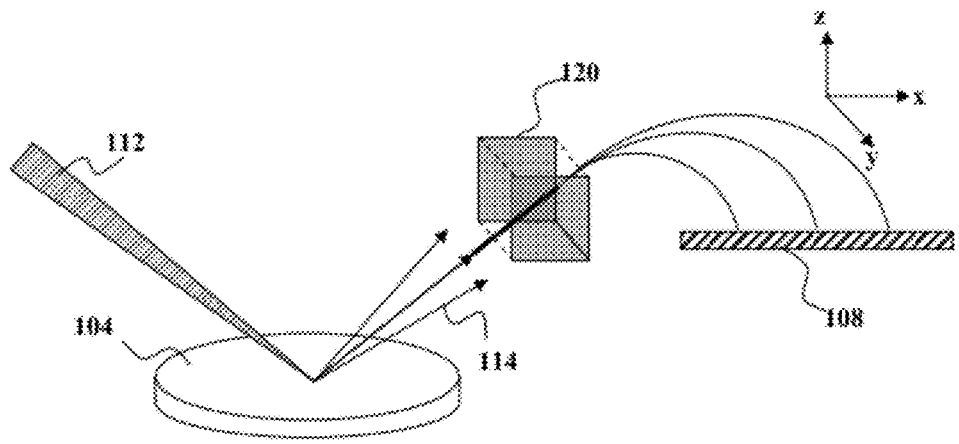
FIG. 2 is a schematic diagram illustrating the focusing effect along the sensor array positioned on the x-axis according to an embodiment of the present invention.

FIG. 2 is a schematic diagram illustrating the focusing effect along the sensor array positioned on the x-axis according to an embodiment of the present invention. In the particular example shown in FIG. 2, a beam of primary radiation 112 (e.g., of electrons, X-rays, ultraviolet radiation, etc.) bombards a defect on the surface of the sample 104. Interaction between the primary radiation 112 and the sample 104 causes secondary electrons 114 to be emitted. By way of example, if the primary radiation 112 is in the form of electrons, the secondary electrons 114 may include Auger electrons.

A portion of the secondary electrons 114 enter the analyzer where they are subjected to a substantially hyperbolic electric field, causing them to land on the detector 108. The hyperbolic field focuses electrons with different azimuthal angles, but the same energy onto the detector 108. The focusing action of the hyperbolic field is generally in the x direction and z direction in FIG. 2, but generally not in a transverse direction y that is perpendicular to the x-z plane. A transverse focusing optic device 120 is positioned on the x-axis and proximate to the entrance aperture of the electron energy analyzer to focus the secondary electrons 114 having transverse velocity components towards the x-z plane. Transverse focusing of the secondary electrons 114 improves detection efficiency and reduces collection time, which improves the throughput of the device. A faster collection time also reduces the amount of contamination that builds up on the sample 104 during spectrum collection. Models of such a device predict improvement in detection efficiency by a factor of 2, which can reduce the collection time by 25-30%. Alternatively, for a fixed detection time, a higher confidence level in defect ID may be achieved.

Figure 3:
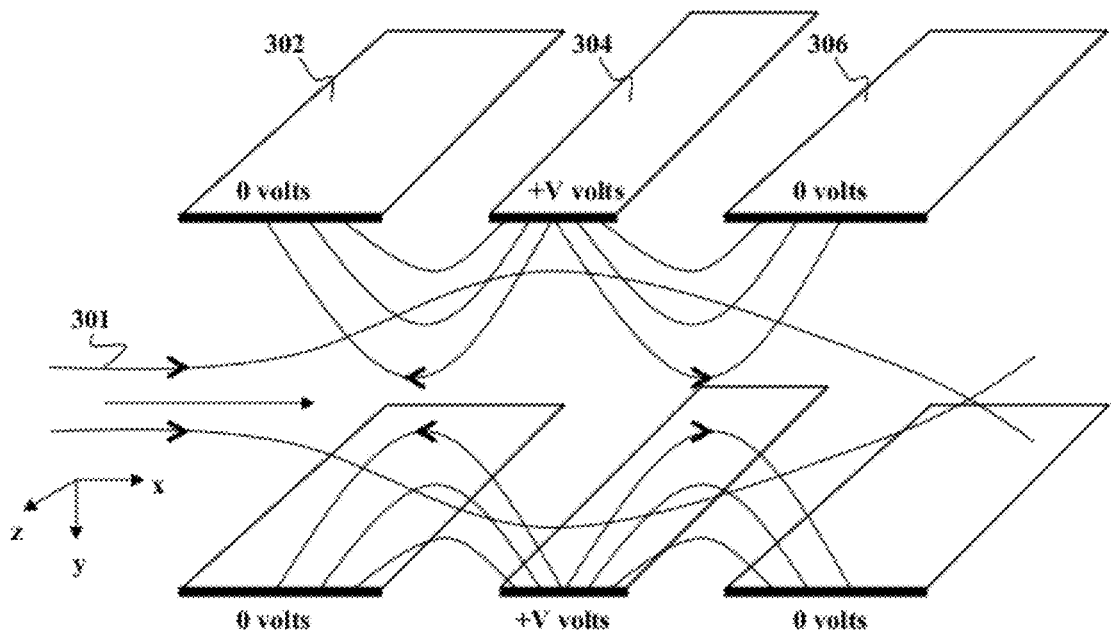
FIG. 3 is a schematic diagram of an Einzel lens that may be used to counter a spread of electron trajectories in a transverse direction in a hyperbolic field energy analyzer according to an embodiment of the present invention.

The focusing optical device 120 is preferably an electrostatic lens, such as an Einzel lens, an example of which is shown in FIG. 3. The Einzel lens consists of three or more pairs of planar electrodes 302, 304, 306 oriented parallel to the focusing plane for the analyzer, e.g., the x-z plane. Charged particles 301 pass sequentially between each pair of electrodes. The middle pair of electrodes 304 is at a different potential than the other two pairs of electrodes 302, 306, which are at the same potential as each other. Each pair of facing electrodes produces electric fields E that deflect charged particles as the pass through. The different voltages on electrodes in adjacent pairs produce fringing fields having components transverse to the electron beam path.

Since the voltages on the outer pairs of electrodes 302, 306 are symmetric with respect to the inner pair 304, the charged particles 301 regain their initial speed upon existing the lens, thus, charged particles exiting the Einzel lens 300 have the kinetic energy with which they entered the Einzel lens. Due to the fields between adjacent pairs of electrodes the velocity of the outer particles may be altered such that particles that are initially diverging away from the focusing plane tend to converge towards the focusing plane. This may cause particles having a greater initial angle of divergence to arrive at the focus intersection slightly later than the ones that travel along a straight path, as they have to travel an extra distance.

Figure 4:
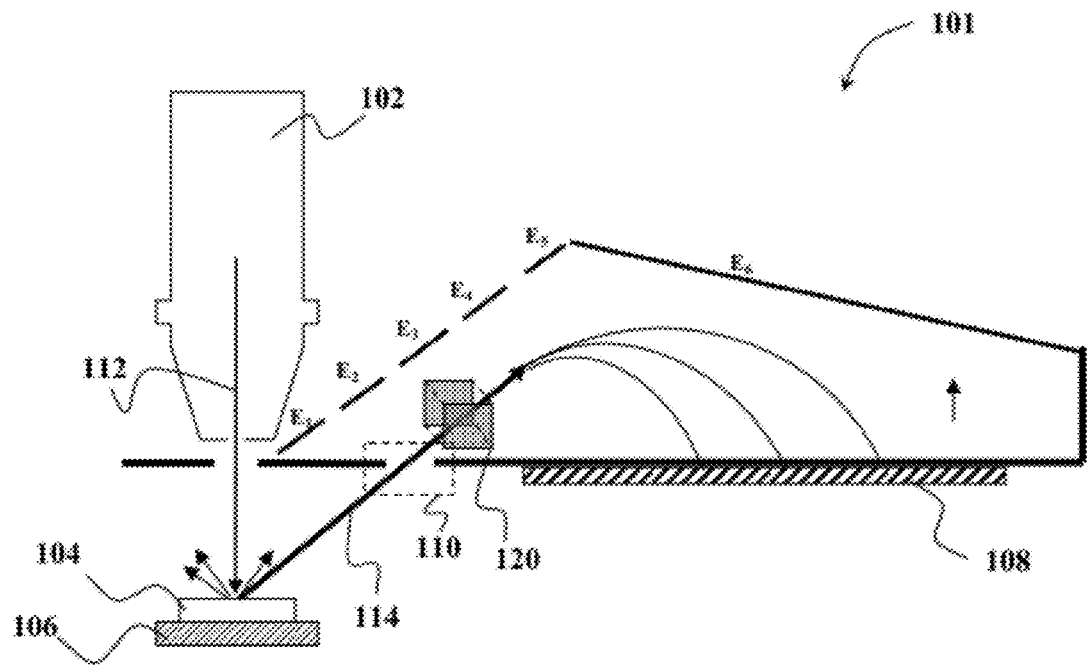
FIG. 4 is a schematic diagram illustrating an optical instrument according to an embodiment of the present invention.

According to an embodiment of the present invention, an instrument for characterizing a defect on a sample may include a transverse focusing optic device positioned inside an electron energy analyzer. For example, as shown in FIG. 4, an instrument 101 may include a focusing optical device 120 positioned proximate the entrance aperture 110 of an electron energy analyzer 100, such as a hyperbolic field analyzer. The transverse focusing device may be positioned inside the hyperbolic field produced by the analyzer 100. In this case, an additional array of electrostatic or magnetic dipoles or other multipoles may be utilized combined with the hyperbolic field, to achieve compression of the electrons in the transverse direction without affecting the dispersion in the primary focusing direction.

Figure 5:
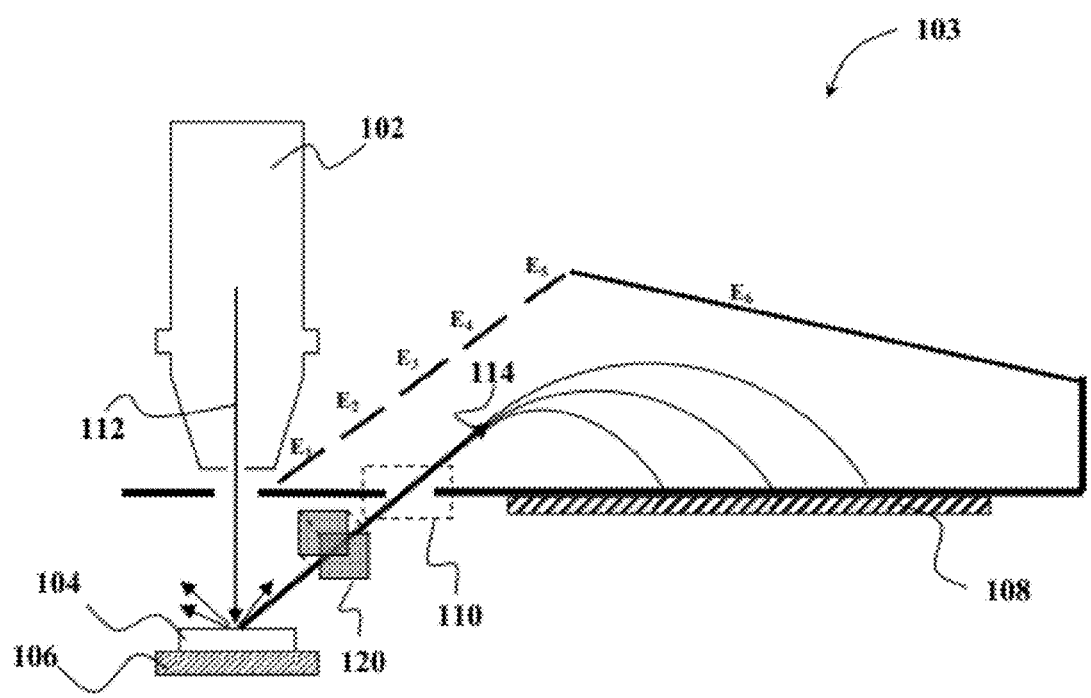
FIG. 5 is a schematic diagram illustrating an optical instrument according to an alternative embodiment of the present invention.

FIG. 5 is a schematic diagram illustrating an optical instrument 103 according to an alternative embodiment of the present invention. The instrument 103 includes a focusing optic device 120 positioned proximate the entrance aperture 110 of the electron energy analyzer 100 and outside the hyperbolic field. In this case the instrument 103 may include an extraction field between the detector 108 and the sample 104, which can be implemented either using cylindrical or multipole optical components.

Figure 6:
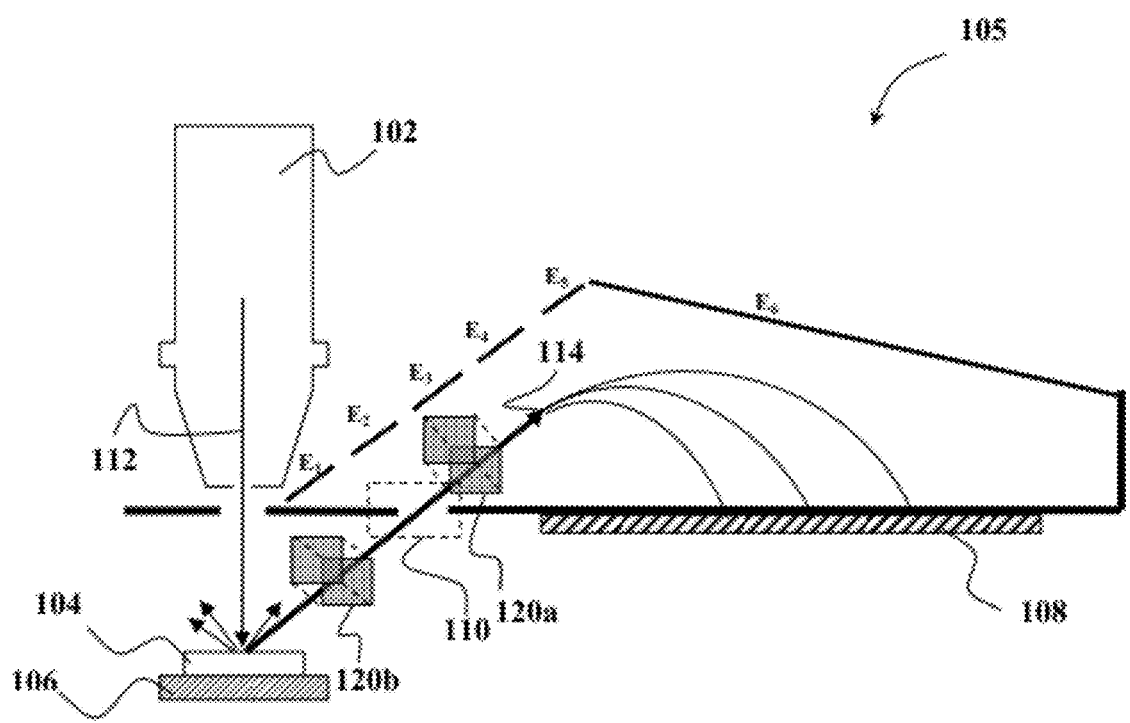
FIG. 6 is a schematic diagram illustrating an optical instrument according to another alternative embodiment of the present invention.

FIG. 6 is a schematic diagram illustrating an optical instrument according to an alternative embodiment of the present invention. The instrument 105 includes a first focusing optic device 120a positioned inside a hyperbolic field electron energy analyzer 100 and inside the hyperbolic field and a second focusing optical device 120b positioned outside of the hyperbolic field. The first and second focusing optical devices 120a, 120b are proximate the entrance aperture 110 of the electron energy analyzer.

In this case, an additional array of dipoles or other multipoles may be utilized in conjunction with the hyperbolic field, to achieve compression of the electrons in the transverse direction without affecting the dispersion in the primary focusing direction and an extraction field between the detector and the sample, which can be implemented either using cylindrical or multipole components.

Embodiments of the present invention allow for greater sensitivity and faster collection times for electron spectroscopy. Such advantages may lead to increased throughput and reduced cost for chemical characterization of defects in semiconductor wafer production and similar substrate processing facilities.

While the above is a complete description of the preferred embodiment of the present invention, it is possible to use various alternatives, modifications, and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. An instrument for characterizing a defect on a sample comprising:
   a primary electron source, configured to direct primary radiation to a measurement location on the sample;
   a position sensitive detector;
   an electrostatic electron energy analyzer configured to collect secondary electrons emitted from the measurement location and focus the secondary electrons in a focusing direction at the position sensitive detector at locations that depend on energies of the secondary electrons; and
   a transverse electrostatic focusing device proximate an entrance aperture of the electron energy analyzer, wherein the transverse focusing device is configured to focus electrons emitted from the measurement location in a transverse direction that is perpendicular to the focusing direction, wherein the transverse electrostatic focusing device includes an electrostatic component positioned inside the electron energy analyzer and configured to produce a transverse electrostatic field inside the electrostatic electron energy analyzer.

2. The instrument of claim 1, wherein the transverse focusing device includes an array of dipoles or multipoles configured to focus trajectories of the secondary electrons in the transverse direction without affecting a dispersion of the electrons in the focusing direction.

3. The instrument of claim 1, further comprising one or more electron optical components positioned between the entrance aperture of the electron energy analyzer and the sample.

4. The instrument of claim 3, wherein the one or more electron optical components are configured to produce an extraction field between the sample and the entrance aperture.

5. The instrument of claim 4, wherein the one or more optical components comprise cylindrical or multipole optical components.

6. The instrument of claim 1, wherein the transverse electrostatic focusing device further includes an additional electrostatic component positioned outside the electron energy analyzer.

7. The instrument in claim 1, wherein the electron energy analyzer comprises a hyperbolic-field electrostatic energy analyzer.

8. The instrument of claim 1, wherein the transverse electrostatic focusing device comprises a transverse focusing Einzel lens.

9. The instrument of claim 8, wherein the Einzel lens includes a first, second, and third pair of parallel plates coaxially aligned with a plane parallel to the focusing direction.

10. A method for characterizing a defect on a sample, comprising:
   a) directing primary radiation from a primary electron source to a measurement location on the sample;
   b) capturing secondary electrons emitted from the measurement location in a focusing direction by an electrostatic electron energy analyzer; and
   c) focusing electrons emitted from the measurement location in a transverse direction that is perpendicular to the focusing direction with a transverse focusing device with a transverse electrostatic focusing device having an electrostatic component positioned inside the electron energy analyzer and configured to produce a transverse electrostatic field inside the electrostatic electron energy analyzer.

11. The method of claim 10, wherein c) includes using a transverse focusing device comprising an array of dipoles or multipoles configured to focus trajectories of the secondary electrons in the transverse direction without affecting a dispersion of the electrons in the focusing direction.

12. The method of claim 10, wherein c) includes using a transverse focusing device comprising a first component located inside the electrostatic electron energy analyzer and a second component located outside the electrostatic electron energy analyzer.

13. The method of claim 10, wherein b) includes using an electron energy analyzer comprising a hyperbolic-field electrostatic energy analyzer.

* * * * *